(12) United States Patent
Sachdeva et al.

(10) Patent No.: US 6,350,120 B1
(45) Date of Patent: Feb. 26, 2002

(54) METHOD AND APPARATUS FOR DESIGNING AN ORTHODONTIC APPARATUS TO PROVIDE TOOTH MOVEMENT

(75) Inventors: Rohit Sachdeva, Plano, TX (US); Rudger Rubbert, Berlin (DE)

(73) Assignee: OraMetrix, Inc., Dallas, TX (US)

( * ) Notice: Subject to any disclaimer, the term of this patent is extended or adjusted under 35 U.S.C. 154(b) by 0 days.

(21) Appl. No.: 09/451,564

(22) Filed: Nov. 30, 1999

(51) Int. Cl.[7] ................................................. A61C 3/00
(52) U.S. Cl. ........................................................ 433/24
(58) Field of Search .............................. 433/6, 24, 213

(56) References Cited

U.S. PATENT DOCUMENTS

| | | |
|---|---|---|
| 3,738,005 A | 6/1973 | Cohen et al. |
| 5,011,405 A | 4/1991 | Lemchen ...................... 433/24 |
| 5,395,238 A | 3/1995 | Andreiko et al. ............. 433/24 |
| RE35,169 E | 3/1996 | Lemchen et al. ............. 433/24 |
| 5,518,397 A | 5/1996 | Andreiko et al. ............. 433/24 |
| 5,533,895 A | 7/1996 | Andreiko et al. ............. 433/24 |
| 5,618,716 A | 4/1997 | Andreiko et al. ............. 433/11 |
| 5,879,158 A | 3/1999 | Doyle et al. .................. 433/24 |
| 5,975,893 A | 11/1999 | Chishti et al. .................. 433/6 |
| 6,068,482 A | 5/2000 | Snow .......................... 433/223 |
| 6,099,314 A | 8/2000 | Kopelman et al. ........... 433/213 |
| 6,217,325 B1 | 4/2001 | Chishti et al. ................. 433/24 |
| 6,227,850 B1 | 5/2001 | Chishti et al. ................. 433/24 |
| 6,227,851 B1 | 5/2001 | Chisti et al. ................... 433/24 |

OTHER PUBLICATIONS

Co–pending U.S. Patent application, Ser. No. 09/560,128, filed Apr. 28, 2000.

*Primary Examiner*—Cary E. O'Connor
(74) *Attorney, Agent, or Firm*—McDonnell Boehnen Hulbert & Berghoff (57) ABSTRACT

A method and apparatus for designing an orthodontic structure to provide tooth movement includes processing that begins by obtaining a three-dimensional digital model of a desired orthodontic structure. The processing continues by generating a zero force arch wire based on the three-dimensional digital model of the desired orthodontic structure. The processing continues by placing brackets on at least some of the plurality of teeth in a zero force position with respect to the zero force arch wire. Having placed the brackets on the desired orthodontic structure, the placement is transferred to a three-dimensional digital model of an actual orthodontic structure. Having transferred the bracket placement, a jig may be formed from the digital model of the actual orthodontic structure with the brackets installed. The jig holds the physical embodiments of the brackets such that the brackets may be placed in the patient's mouth in the position determined by the automated process.

30 Claims, 6 Drawing Sheets

METHOD AND APPARATUS FOR DESIGNING AN ORTHODONTIC APPARATUS TO PROVIDE TOOTH MOVEMENT

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that designs an orthodontic apparatus thereby enabling a scientific approach to orthodontics throughout the treatment, maintaining treatment costs, and providing a more consistent treatment time.

DETAILED DESCRIPTION OF A PREFERRED EMBODIMENT

Generally, the present invention provides a method and apparatus for designing an orthodontic structure to provide tooth movement. Such a method and apparatus includes processing that begins by obtaining a three-dimensional digital model of a desired orthodontic structure. The orthodontic structure includes a plurality of teeth that have been positioned into a desired location. The processing continues by generating a zero force arch wire based on the three-dimensional digital model of the desired orthodontic structure. The processing continues by placing brackets on at least some of the plurality of teeth in a zero force position with respect to the zero force arch wire. Having placed the brackets on the desired orthodontic structure, the placement is transferred to a three-dimensional digital model of an actual orthodontic structure. Having transferred the bracket placement, a jig may be formed from the digital model of the actual orthodontic structure with the brackets installed. The jig holds the physical embodiments of the brackets such that the brackets may be placed in the patient's mouth in the position determined by the automated process. With such a method and apparatus, the practice of orthodontics is transformed from an art to a science throughout the treatment process, reduces costs, and provides for more consistent treatment times.

Figure 1:
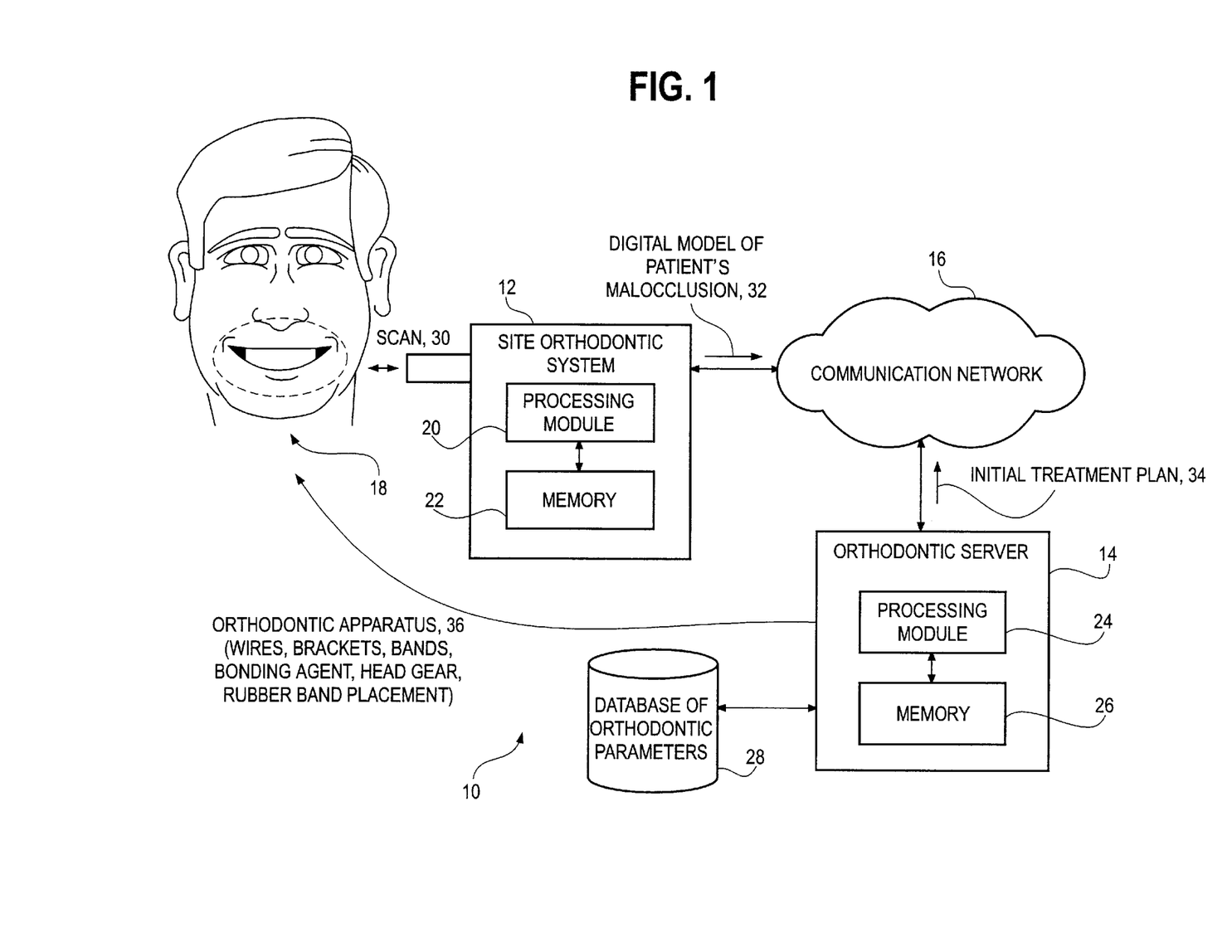
FIG. 1 illustrates a schematic block diagram of an orthodontic system in accordance with the present invention.

The present invention can be more fully described with reference to FIGS. 1 through 6. FIG. 1 illustrates a schematic block diagram of an orthodontic system 10 that includes a site orthodontic system 12, an orthodontic server 14, and a communication network 16. The site orthodontic system 12 includes a processing module 20 and memory 22. The orthodontic server 14 includes a processing module 24 and memory 26. Each of the processing modules 20 and 24 may be an individual processing device or a plurality of processing devices. Such a processing device may be a microprocessor, microcontroller, digital signal processor, microprocessor, central processing unit, state machine, logic circuit, and/or any device that manipulates signals (e.g., analog and/or digital) based on operational instructions. Each of the memory 22 and 26 may be an individual memory device or a plurality of memory devices. Such a memory device may be a read-only memory, floppy disk memory, random access memory, volatile memory, non-volatile memory, and/or any device that stores digital information. Note that when the processing module 20 and/or 24 implement one or more of its functions via a state machine or logic circuitry, the memory storing the corresponding operational instructions is embedded within the circuitry comprising the state machine and/or logic circuit.

In operation, an orthodontic patient 18 has its orthodontic structure scanned 30 via the site orthodontic system 12. The scanning may be done utilizing a white light source, laser, ultrasound, and/or any device to obtain a video image, or surface image, of the orthodontic structure of the patient 18. The site orthodontic system 12 processes the video image to produce a digital model of the patient's malocclusion 32 (i.e., a three-dimensional digital model of the patient's actual orthodontic structure). The site orthodontic system 12 transmits the digital model of the patient's malocclusion 32 to the orthodontic server 14 via the communication network 16. The orthodontic server 14, in accordance with an initial treatment plan 34, designs an orthodontic apparatus 36 based on the digital model of the patient's malocclusion 32, a digital model of a desired orthodontic structure, and orthodontic parameters contained within the database of the orthodontic parameters 28. The orthodontic apparatus 36 may include one or more of wires, brackets, bands, bonding agent, headgear, rubber band placement, and/or auxiliary apparatus.

For a more detailed discussion of the site orthodontic system 12 and the orthodontic server 14 refer to co-pending patent application having a Ser. No. 09/451,560, entitled METHOD AND APPARATUS FOR TREATING AN ORTHODONTIC PATIENT, having a filing date the same as the present patent application, and is assigned to the same assignee as the present patent application. For a detailed discussion of generating the digital model of the actual orthodontic structure refer to co-pending patent application having a Ser. No. 09/452,034, entitled METHOD AND APPARATUS FOR PRODUCING A THREE-DIMENSIONAL IMAGE OF AN ORTHODONTIC PATIENT, having a filing date the same as the present patent application, and is assigned to the same assignee as the present patent application. For a detailed discussion of generating the digital model of the desired orthodontic structure refer to co-pending patent application having Ser. No. 09/452,031, entitled METHOD AND APPARATUS FOR GENERATING A DESIRED THREE-DIMENSIONAL DIGITAL MODEL OF AN ORTHODONTIC STRUCTURE, having a filing date the same as the present patent application, and is assigned to the same assignee as the present patent application.

Figure 2:
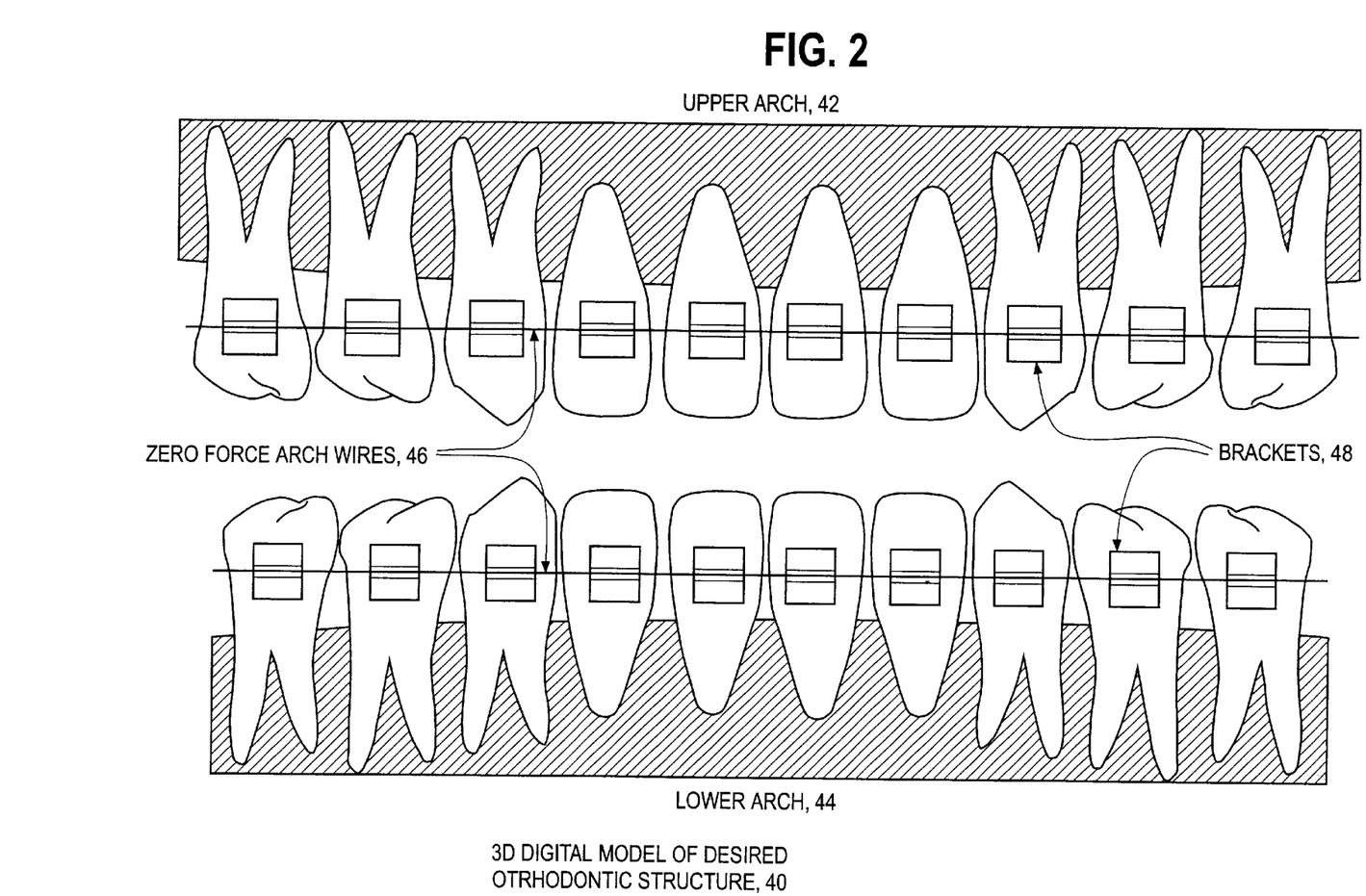
FIG. 2 illustrates a graphical diagram of a three-dimensional digital model of a desired orthodontic structure in accordance with the present invention.

To design the orthodontic apparatus 36, the orthodontic server 14 utilizes a three-dimensional digital model of a desired orthodontic structure. Such a three dimensional digital model of a desired orthodontic structure is shown in FIG. 2. The desired orthodontic structure 40 includes an upper arch 42 and a lower arch 44. In this digital model 40, the teeth are positioned in the desired location.

With the teeth in their ideal, or desired location, a zero force arch wire 46 is generated for the upper arch 42 and lower arch 44 with respect to the depths of the slot. Alternatively, the arch wires may be generated with respect to the reference line joining the idealized contact point of the teeth, cusp tips, the inner surface of the teeth, or the outer surface of the teeth. In these alternatives, the size of the bracket and of the teeth need to be factored into generating the zero force arch wires. In the simplest form, the zero force arch wire 46 will have a simple arch shape such that each arch wire's shape will correspond to the upper arch 42 and the lower arch 44, respectively. With the zero force arch wire 46 installed in the upper arch 42, the brackets 48 for the upper teeth are positioned such that a zero force (i.e., a sub-threshold force or a force insufficient to move a tooth) is provided between the zero force arch wire 46 and the bracket. As shown, each of the brackets 48, in the upper arch have the slots aligned such that the zero force arch wire 46 of the upper arch 42 resides in the slots without providing a force upon any of the teeth. A similar arrangement is done for the lower arch 44. Note that this processing is being performed by the orthodontic server 14 as a computer simulation.

As one of average skill in the art would appreciate, the zero force arch wire 46 may have bends in three planes of space when the brackets are not placed in the ideal linear fashion or due to anatomical limitations of a tooth or teeth (e.g., a small tooth not being able to support a bracket in the ideal location). For instance, if the brackets are installed and the actual position is not as shown in FIG. 2, the wire 46 may be designed, and subsequently fabricated, with bends to accommodate for the misplaced brackets 48. The bends and the slides are determined based on the size of the tooth, or teeth, and the size of the brackets. In addition, the wires may have bends to provide an additive force system, a negative force system, and may further includes loops to provide additional displacement, or retention, forces.

Figure 3:
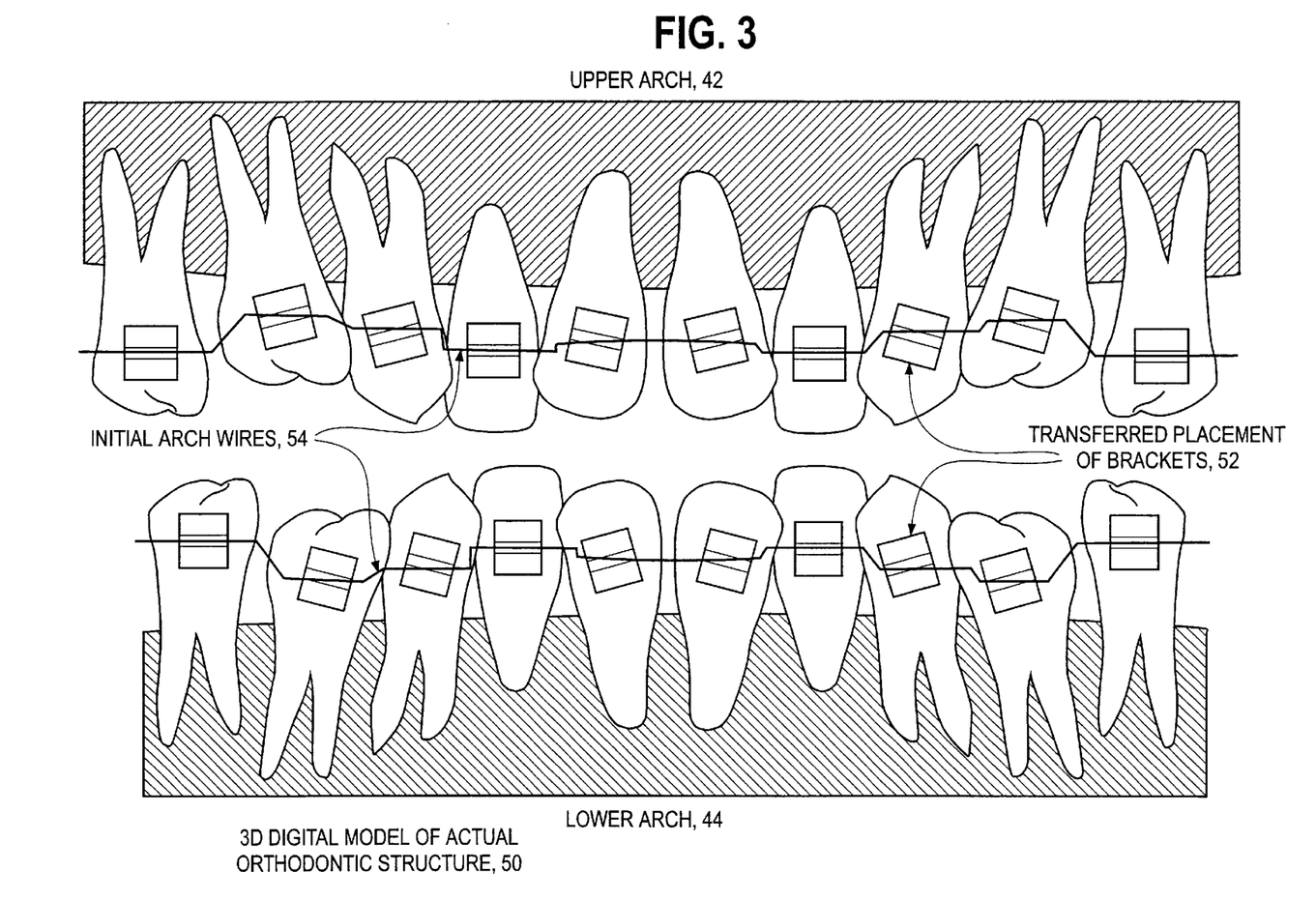
FIG. 3 illustrates a graphical diagram of a three-dimensional digital model of an actual orthodontic structure in accordance with the present invention.

FIG. 3 illustrates a three dimensional model of an actual orthodontic structure 50. In this illustration, the placement of the brackets on the teeth in the three-dimensional digital model of the desired orthodontic structure 40 has been transferred to the three-dimensional digital model of the actual orthodontic structure 50. As shown, each positioning of the bracket, on a per tooth basis, corresponds to the positioning of the bracket in the illustration of FIG. 2. However, since each of the teeth is misaligned, the resulting bracket orientation for the actual orthodontic structure 50 is as shown in FIG. 3. Having transferred the bracket placement 52 for the upper arch 42 and the lower arch 44, an initial arch wire 54 is designed, and subsequently fabricated, for the upper arch 42 and the lower arch 44. The initial arch wire 54 may be the zero force arch wire 46 or the first of a series of arch wires where the zero force arch wire is the last wire in the series. Note that whether one or more arch wires will be required for treatment is dependent upon the degree of malocclusion. For a more severe malocclusion, multiple arch wires may be required. In addition, the type of arch wire may affect the number of arch wires used. For example, a super elastic arch wire may only require one or two arch wires to be fabricated where less elastic arch wires may require multiple arch wires. Such determinations as to which type of arch wire to use can be programmed into the system, selected by the practitioner utilized the orthodontic system 10, and/or based on cost factors, patient pain tolerance, patient commitment, bio-physical characteristics of the patient (e.g., can the patient's teeth be moved using a particular arch wire), mechanical characteristics of the wire, dimensional characteristics of the brackets, slots, and wire, and any other factors that contribute to orthodontic treatment.

Figure 4:
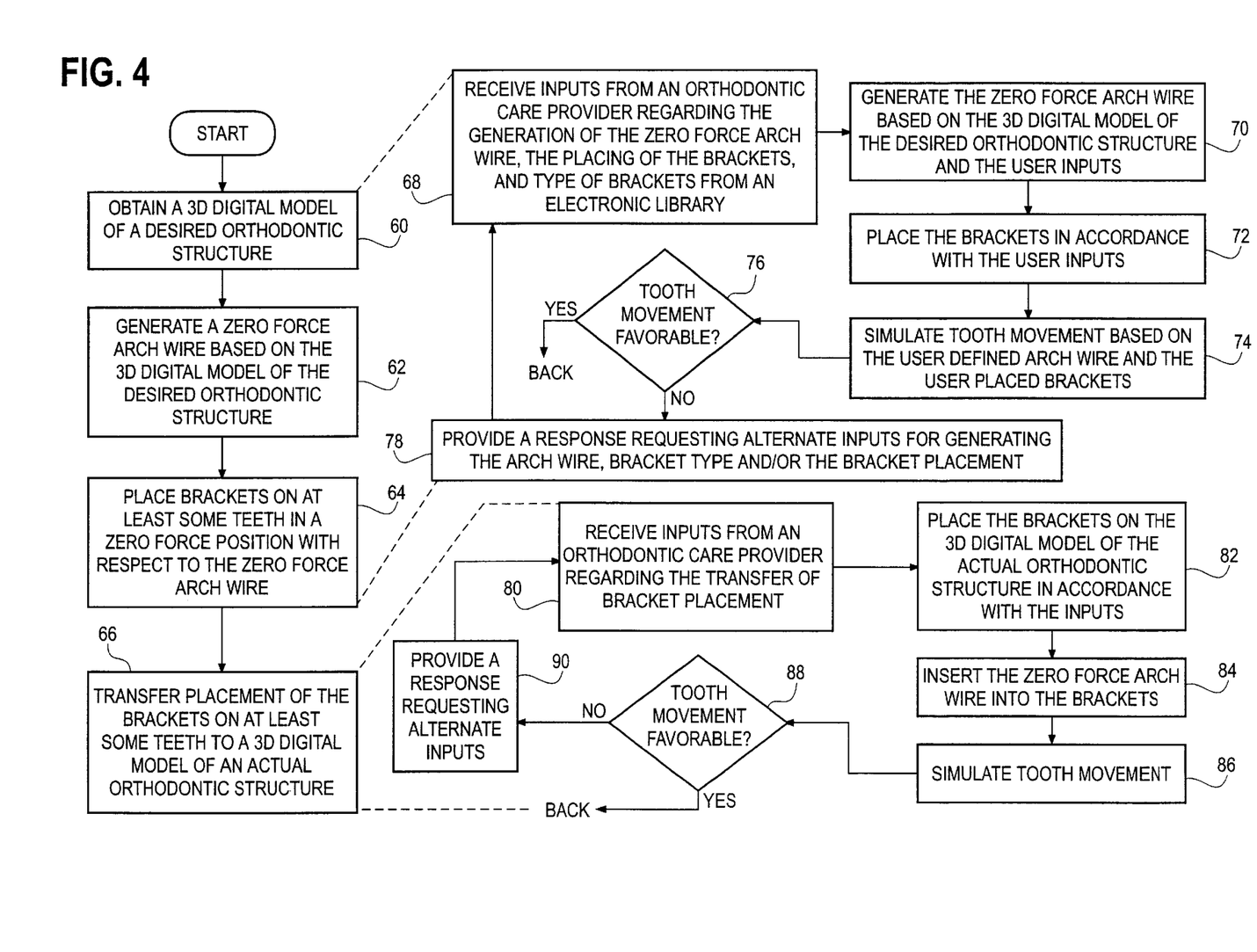
FIG. 4 illustrates a logic diagram of a method for designing an orthodontic apparatus to provide tooth movement in accordance with the present invention.

FIG. 4 illustrates a logic diagram of a method for designing an orthodontic apparatus to provide tooth movement. The processing steps of FIG. 4 may be implemented as operational instructions and stored in memory 22 and/or 26 and executed by processing modules 20 and/or 24. The process begins at step 60 where a three-dimensional digital model of a desired orthodontic structure is obtained. The process then proceeds to step 62 where a zero force arch wire is generated for each arch based on the three-dimensional digital model of the desired orthodontic structure. The process then proceeds to step 64 where the brackets are placed on at least some of the teeth in a zero force position with respect to the zero force arch wire. This was illustrated in FIG. 2. The process then proceeds to step 66 where placement of the brackets on at least some of the teeth is transferred to the three-dimensional digital model of the actual orthodontic structure.

The processing steps 62 and 64 may in turn include steps 68 through 78. At step 68 inputs are received from an orthodontic care provider regarding the generation of the zero force arch wire, the placement of the brackets, and type of brackets to use (standard bracket, prescription bracket, custom bracket from various vendors), which may be selected from an electronic library of brackets. Accordingly, the orthodontic system 10 may be providing an interactive process with an orthodontic care provider to design the zero force arch wire. Alternatively, the generation of the zero force arch wire may be done in a completely automated fashion.

The processing then continues to step 70 where the zero force arch wire is generated based on the three-dimensional digital model of the desired orthodontic structure and the user inputs received at step 68. The process then proceeds to step 72 where the brackets are placed on the three-dimensional digital model of the actual orthodontic structure in accordance with the user inputs. The process then proceeds to step 74 where tooth movement is simulated based on the user defined arch wire and the user placed brackets. Such a simulation will be based on orthodontic parameters of the patient and orthodontic parameters of the orthodontic apparatus. For example, such orthodontic parameters may include crown morphology, gum morphology, tooth size, age, gender of the patient, sex of the patient, race of the patient, where the orthodontic parameters of the orthodontic apparatus include bracket size, wire size, wire elasticity and other mechanical properties of the orthodontic apparatus. In essence, the simulation of tooth movement has the user defined arch wire installed into the three-dimensional digital model of the actual orthodontic structure having the user placed brackets thereon. Utilizing elasticity characteristics of the user defined arch wire, the teeth movement is simulated to provide zero force between the arch wire and the user placed brackets.

The process then proceeds to step 76 where a determination is made as to whether the tooth movement is favorable. Favorable tooth movement may be determined in an automated process in that the resulting structure substantially matches the three-dimensional digital model of the desired orthodontic structure or based on inputs received from the orthodontic care provider. Such inputs from the orthodontic care provider may indicate that the orthodontic care provider accepts the positioning of the teeth. If, however, the tooth movement is not favorable, the process proceeds to step 78 where a response is provided requesting alternate inputs for generating the arch wire, selecting another bracket type from a library of digital brackets, designing a new bracket, and/or the bracket placement.

Step 66 of FIG. 4 may further include the processing steps of 80 through 90. At step 80, inputs from an orthodontic care provider are received regarding the transfer of bracket placement. The process then proceeds to step 82 where the brackets are placed on the three-dimensional digital model of the actual orthodontic structure in accordance with the inputs. The process then proceeds to step 84 where the zero force arch wire is inserted into the brackets. The process then proceeds to step 86 where tooth movement is simulated. The process then proceeds to step 88 where a determination is made as to whether tooth movement was favorable. If not, the process proceeds to step 90 where a response is provided requesting alternate inputs. The process then loops back to step 80.

Figure 5:
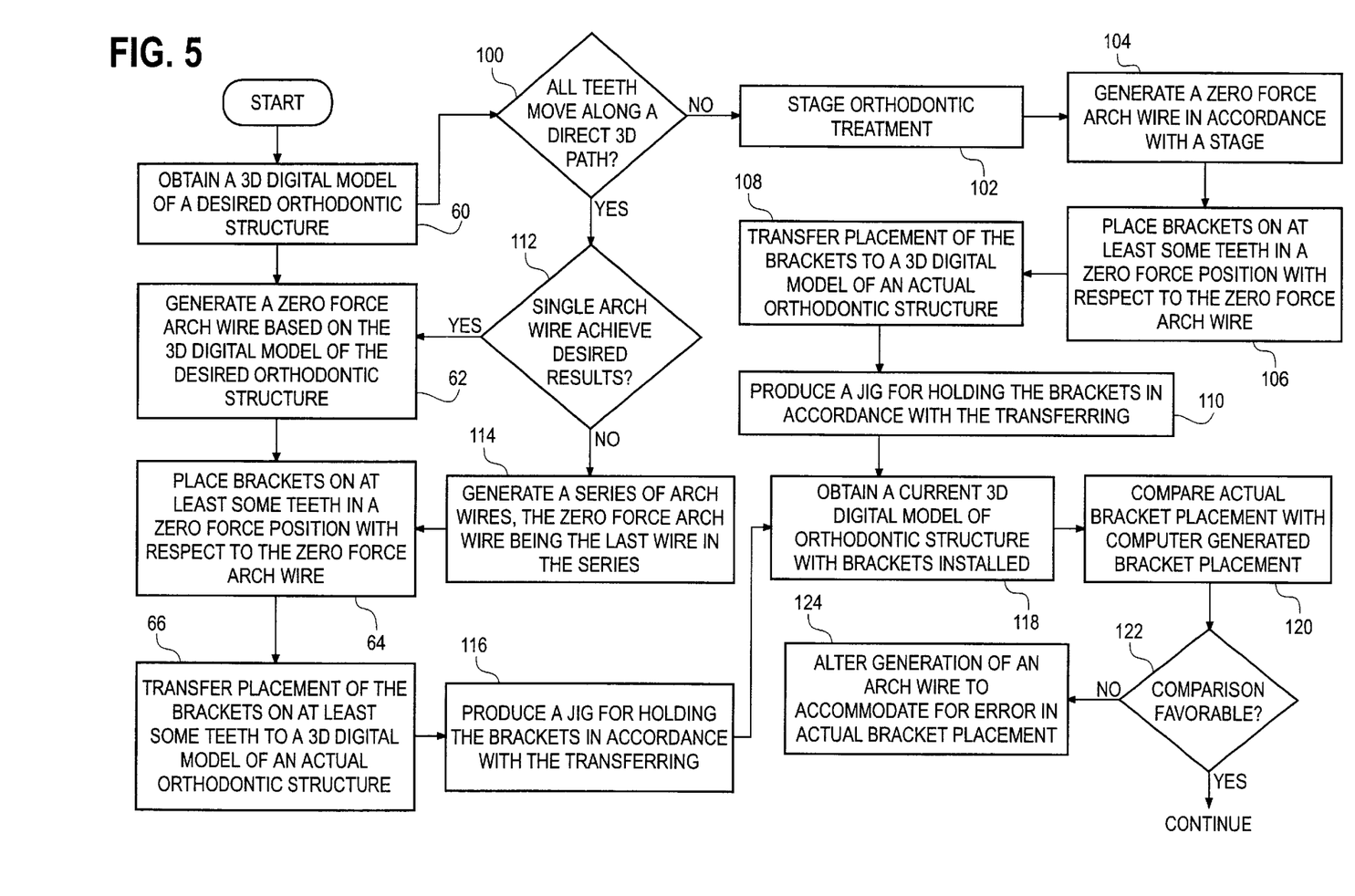
FIG. 5 illustrates a logic diagram of an alternate method for designing an orthodontic apparatus to provide tooth movement in accordance with the present invention.

FIG. 5 illustrates a logic diagram of an alternate method for designing an orthodontic apparatus to provide tooth movement. The process begins at step 60 where a three dimensional digital model of a desired orthodontic structure is obtained. The process then proceeds to step 100 where a determination is made as to whether all teeth move along a three-dimensional path. For a detailed discussion of determining whether the teeth move along the three-dimensional path refer to co-pending patent application having Ser. No. 09/451,609, entitled METHOD AND APPARATUS FOR SIMULATING TOOTH MOVEMENT FOR AN ORTHODONTIC PATIENT, now U.S. Pat. No. 6,250,918, having a filing date the same as the present patent application, and is assigned to the same assignee as the present patent application.

If all the teeth move along the direct three-dimensional path, the process proceeds to step 112 where a determination is made as to whether a single arch wire can achieve the desired results. If so, the process reverts to step 62 where the zero force arch wire is generated. If a single arch wire will not achieve the desired results, the process proceeds to step 114 where a series of arch wires are generated where the zero force arch wire is the last in the series. Each wire may include bends, loops, slide positioning, and/or other geometric shape to provide a determined amount of tooth movement or tooth anchoring. Having generated the series of wires, the process proceeds to step 64 where the brackets, bands, and/or any other orthodontic structures, are placed on at least some of the teeth in accordance with a zero force position. Note that, depending on the stage of treatment, not all of the teeth may have brackets and/or bands installed thereon. The process then proceeds to step 66 where the placement of the bracket is transferred to a three-dimensional digital model of an actual orthodontic structure. The process then proceeds to step 116 where a jig is produced for holding the brackets in accordance with the transferring step of 66.

The process then proceeds to step 118 where a current three-dimensional digital model of the orthodontic structure containing the brackets is obtained. Note that step 118 may be done after the initial installation of the brackets or at any time throughout the treatment. The process then proceeds to step 120 where the actual bracket placement is compared with the computer generated ideal bracket placement. The computer generated ideal bracket placement is illustrated and discussed with reference to FIG. 2. Alternatively, the comparison may be done by inserting the zero force arch wire in the current three-dimensional digital model and determining whether the corresponding computer generated digital model is obtained. Note that if a series of wires is generated, the computer generated response would correspond to the particular wire in the series of wires being used.

The process then proceeds to step 122 where a determination is made as to whether the comparison was favorable. If so, the process continues to the next step in the initial treatment plan. Note that the orthodontic treatment may be updated to include newer technologies. When this occurs, the processes of steps 118 through 122 are repeated in accordance with the newer technologies.

If the comparison was unfavorable, the process the proceeds to step 124 where generation of at least one arch wire is altered to accommodate for the error in the actual bracket placement. As such, if a bracket were placed such that when the teeth are in the ideal position, as shown in FIG. 2, one of the slots is not aligned with the other slots, the zero force wire may be bent to still provide zero force through that bracket. In addition, a determination may be done as to whether the altering of the arch wire may be sufficient to achieve the desired results. If not, an auxiliary appliance may be required. Such an auxiliary appliance may be to anchor a tooth, or teeth, provide a cross arch wire, a spring wire, and/or a repositioning structure.

Figure 6:
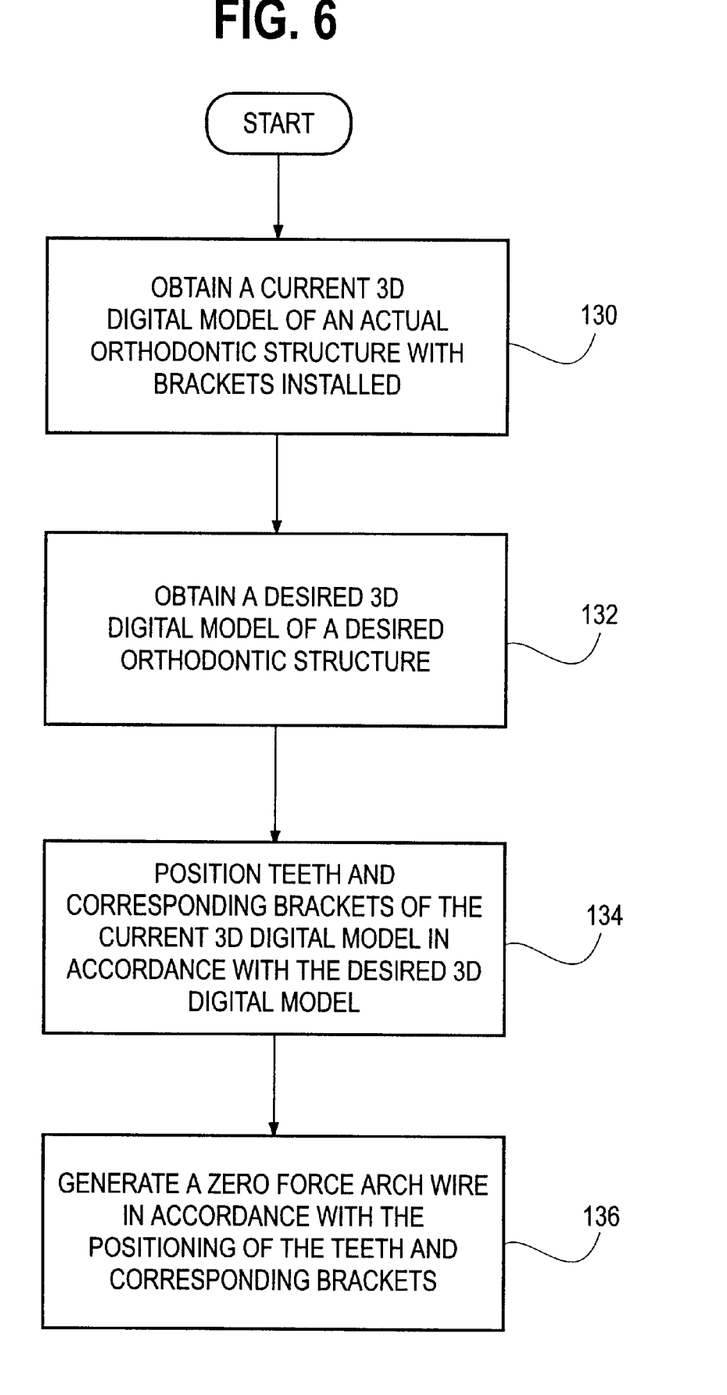
FIG. 6 illustrates a logic diagram of yet another alternate method for designing an orthodontic apparatus to provide tooth movement in accordance with the present invention.

FIG. 6 illustrates a logic diagram of another alternate method for designing orthodontic apparatus. The process begins at step 130 where a current three-dimensional digital model of an actual orthodontic structure is obtained. The current three-dimensional model includes the brackets. The process then proceeds to step 132 where a desired three-dimensional digital model of a desired orthodontic structure is obtained. The process proceeds to step 134 where the teeth and corresponding brackets of the current three-dimensional model are positioned in accordance with the desired three-dimensional digital model. In other words, the teeth with their brackets fixed thereto are repositioned into the desired tooth position as shown in FIG. 2. Note that this may be done as an automated process or based on user inputs. The process then proceeds to step 136 where a zero force arch wire is generated in accordance with the positioning of the teeth and the corresponding brackets in the desired positions.

The preceding discussion has presented a method and apparatus for designing an orthodontic apparatus to provide tooth movement. By utilizing the teachings of the present invention, the practice of orthodontics is being converted from an art to a science. In essence, by utilizing the three-dimensional digital models to simulate tooth movement and bracket placement, the accuracy of orthodontic treatment is substantially increased. Note that the use of the term bracket may be inclusive of brackets and/or bands. Further note that a wire may be mechanically bent, thermally manipulated, and/or a combination thereof. Still further note a wire may be a customized composite wire, have various cross section dimensions, and/or of various elasticity. As one of average skill in the art would appreciate, other embodiments may be derived from the teachings of the present invention without deviating from the scope of the claims.

What is claimed is:

1. A method for designing an orthodontic apparatus to provide tooth movement, the method comprises the steps of:
   a) obtaining a three-dimensional digital model of a desired orthodontic structure that includes a plurality of teeth each positioned in a desired location;
   b) simulating an arch wire based on the three-dimensional digital model of the desired orthodontic structure which would exert substantially zero forces on the teeth when the teeth are positioned in the desired location;

c) simulating placing brackets on at least some of the plurality of teeth in a zero force position with respect to the arch wire; and d) simulating a transferring of the placement of the brackets on the at least some of the teeth to a three-dimensional digital model of an actual orthodontic structure.

2. The method of claim 1, wherein steps (b) and (c) further comprise:

receiving inputs from an orthodontic care provider regarding the generating of the arch wire, the placing of the brackets, and type of bracket from an electronic library;

simulating the arch wire in accordance with the inputs to produce a user defined arch wire;

simulating placing the brackets in accordance with the inputs to produce user placed brackets;

simulating tooth movement based on the user defined arch wire and the user placed brackets; and when the simulating of the tooth movement is not favorable, providing a response requesting alternate inputs for at least one of: generating the arch wire and the placing of the brackets.

3. The method of claim 1, wherein step (d) further comprises:

receiving inputs from an orthodontic care provider regarding the transferring the placement of the brackets;

simulating placing the brackets on the three-dimensional digital model in accordance with the inputs to produce user transferred bracket placement;

simulating inserting the arch wire into the brackets;

simulating tooth movement; and when the simulating of the tooth movement is not favorable, providing a response requesting alternate inputs.

4. The method of claim 1 further comprising:

determining whether each of the plurality of teeth move along a direct three-dimensional path;

when at least one tooth does not move along a corresponding direct three-dimensional path, staging orthodontic treatment in a plurality of stages of tooth movement steps; and simulating placing the brackets on the three-dimensional digital model of the desired orthodontic structure in accordance with the staging of the orthodontic treatment; and producing a jig for holding the brackets in accordance with the transferring placement of the brackets, wherein the jig enables an orthodontic care provider to accurately install the brackets.

5. The method of claim 4, wherein the staging the orthodontic treatment comprises at least one of: initially moving a priority tooth and subsequently moving other teeth, initially aligning several teeth and subsequently utilizing the several teeth as an anchor for moving another tooth, and moving at least one tooth along an indirect path.

6. The method of claim 4 further comprising:

obtaining a current three-dimensional digital model of the orthodontic structure with the brackets installed;

comparing the current three-dimensional digital model with a simulated three-dimensional digital model with the brackets installed;

when the comparing is unfavorable, simulating altering an arch wire to accommodate for a difference between bracket placement in the current three-dimensional digital model with the simulated three-dimensional digital model.

7. The method of claim 6, wherein the comparing step comprises:

simulating inserting the arch wire into the brackets of the current three-dimensional digital model;

simulating tooth movement; and determining whether the simulating tooth movement produced the desired orthodontic structure.

8. The method of claim 6 further comprising at least one of:

obtaining the current three-dimensional digital model after initial installation of the brackets; and obtaining the current three-dimensional digital model during orthodontic treatment.

9. The method of claim 6 further comprising:

determining whether the altering of the arch wire will provide adequate correction; and when the altering of the arch wire will not provide adequate correction, simulating generating an auxiliary appliance.

10. The method of claim 4 further comprising:

determining whether orthodontic treatment is to be changed due to newer technology; and when the orthodontic treatment is to be changed due to newer technology, updating the three-dimensional digital models in accordance with the newer technology.

11. The method of claim 4 further comprising:

when each of the plurality of teeth moves along a direct three-dimensional path, determining whether a single arch wire can achieve the desired orthodontic structure; and when the single arch wire cannot achieve the desired orthodontic structure, designing a series of arch wires.

12. The method of claim 11 wherein the step of determining whether the single arch wire can achieve the desired orthodontic structure comprises at least one of:

determining per tooth distance of movement;

determining delamination forces;

determining wire and bracket receptacle coupling;

determining allowable per tooth force; and determining patient pain tolerance.

13. A method for designing an orthodontic apparatus to provide tooth movement, the method comprises the steps of:

a) obtaining a current three-dimensional digital model of an orthodontic structure with brackets installed on the orthodontic structure;

b) obtaining a desired three-dimensional digital model of a desired orthodontic structure;

c) simulating positioning of the teeth and the corresponding brackets of the current three-dimensional digital model in accordance with the desired three-dimensional digital model; and d) simulating an arch wire in accordance with the positioning of the teeth and the corresponding brackets which would exert substantially zero forces on the teeth when the teeth are positioned in a desired location in the desired orthodontic structure.

14. The method of claim 13, wherein steps (c) and (d) further comprise:

receiving inputs from an orthodontic care provider regarding the generating of the arch wire and the positioning of the teeth and the corresponding brackets;

simulating the arch wire in accordance with the inputs to produce a user defined arch wire;

simulating tooth movement based on the user defined arch wire and the user placed brackets; and when the simulating of the tooth movement is not favorable, providing a response requesting alternate inputs for at least one of: generating the arch wire, selecting a different bracket from a library of digital brackets, designing a new bracket, and the placing of the brackets.

15. The method of claim 13 further comprising:

determining whether each of the plurality of teeth move along a direct three-dimensional path; and when at least one tooth does not move along a corresponding direct three-dimensional path, staging orthodontic treatment; and producing a jig for holding the brackets in accordance with the transferring placement of the brackets, wherein the jig enables an orthodontic care provider to accurately install the brackets.

16. The method of claim 15 further comprising:

when each of the plurality of teeth move along a direct three-dimensional path, determining whether a single arch wire can achieve the desired orthodontic structure; and when the single arch wire cannot achieve the desired orthodontic structure, designing a series of arch wires.

17. An apparatus for designing an orthodontic apparatus to provide tooth movement, the apparatus comprising:

a processing module; and memory operably coupled to the processing module, wherein the memory stores operational instructions that cause the processing module to: (a) obtain a three-dimensional digital model of a desired orthodontic structure that includes a plurality of teeth each positioned in a desired location; (b) generate a simulated arch wire based on the three-dimensional digital model of the desired orthodontic structure which would exert substantially zero forces on the teeth when the teeth are positioned in the desired location; (c) simulate the placement of brackets on at least some of the plurality of teeth in a zero force position with respect to the arch wire; and (d) simulate a transfer of the placement of the brackets on the at least some of the teeth to a three-dimensional digital model of an actual orthodontic structure.

18. The apparatus of claim 17, wherein the memory further comprises operational instructions that cause the processing module to generate the arch wire and to place the brackets by:

receiving inputs from an orthodontic care provider regarding the generating of the arch wire, the placing of the brackets, and type of bracket from an electronic library;

generating the arch wire in accordance with the inputs to produce a user defined arch wire;

placing the brackets in accordance with the inputs to produce user placed brackets;

simulating tooth movement based on the user defined arch wire and the user placed brackets; and when the simulating of the tooth movement is not favorable, providing a response requesting alternate inputs for at least one of: generating the arch wire and the placing of the brackets.

19. The apparatus of claim 17, wherein the memory further comprises operational instructions that cause the processing module to simulate the transfer the placement of the brackets by:

receiving inputs from an orthodontic care provider regarding the transferring the placement of the brackets;

simulate placing the brackets on the three-dimensional digital model in accordance with the inputs to produce user transferred bracket placement;

simulate inserting the arch wire into the brackets;

simulating tooth movement; and when the simulating of the tooth movement is not favorable, providing a response requesting alternate inputs.

20. The apparatus of claim 17, wherein the memory further comprises operational instructions that cause the processing module to:

determine whether each of the plurality of teeth move along a direct three-dimensional path;

when at least one tooth does not move along a corresponding direct three-dimensional path, stage orthodontic treatment; and simulate the placement of the brackets on the three-dimensional digital model of the desired orthodontic structure in accordance with the staging of the orthodontic treatment.

21. The apparatus of claim 20, wherein the memory further comprises operational instructions that cause the processing module to:

when each of the plurality of teeth moves along a direct three-dimensional path, determine whether a single arch wire can achieve the desired orthodontic structure; and when the single arch wire cannot achieve the desired orthodontic structure, design a series of arch wires.

22. The apparatus of claim 21, wherein the memory further comprises operational instructions that cause the processing module to determine whether the single arch wire can achieve the desired orthodontic structure by at least one of:

determining per tooth distance of movement;

determining delamination forces;

determining wire and bracket receptacle coupling;

determining allowable per tooth force; and determining patient pain tolerance.

23. The apparatus of claim 20, wherein the memory further comprises operational instructions that cause the processing module to:

obtain a current three-dimensional digital model of the orthodontic structure with the brackets installed;

compare the current three-dimensional digital model with a simulated three-dimensional digital model with the brackets installed;

when the comparing is unfavorable, alter generating of an arch wire to accommodate for a difference between bracket placement in the current three-dimensional digital model with the simulated three-dimensional digital model.

24. The apparatus of claim 23, wherein the memory further comprises operational instructions that cause the processing module to compare the current three-dimensional digital model with a simulated three-dimensional digital model with the brackets installed by:

simulating inserting the arch wire into the brackets of the current three-dimensional digital model;

simulating tooth movement; and determining whether the simulating tooth movement produced the desired orthodontic structure.

25. The apparatus of claim 23, wherein the memory further comprises operational instructions that cause the processing module to obtain the current three-dimensional digital model of the orthodontic structure by at least one of:
  obtaining the current three-dimensional digital model after initial installation of the brackets; and
  obtaining the current three-dimensional digital model during orthodontic treatment.

26. The apparatus of claim 23, wherein the memory further comprises operational instructions that cause the processing module to:
  determine whether the altering of the arch wire will provide adequate correction; and
  when the altering of the arch wire will not provide adequate correction, simulating generating an auxiliary appliance.

27. An apparatus for designing an orthodontic apparatus to provide tooth movement, the apparatus comprises:
  a processing module; and
  memory operably coupled to the processing module, wherein the memory stores operational instructions that cause the processing module to: (a) obtain a current three-dimensional digital model of an orthodontic structure with brackets installed; (b) obtain a desired three-dimensional digital model of a desired orthodontic structure; (c) simulate the positioning of teeth and corresponding brackets of the current three-dimensional digital model in accordance with the desired three-dimensional digital model; and (d) generate a simulated arch wire in accordance with the positioning of the teeth and corresponding brackets which would exert substantially zero forces on the teeth when the teeth are positioned in a desired location in the desired orthodontic structure.

28. The apparatus of claim 27, wherein the memory further comprises operational instructions that cause the processing module to position the teeth and generate the arch wire by:
  receiving inputs from an orthodontic care provider regarding the generating of the arch wire and the positioning of the teeth and the corresponding brackets;
  generating a simulation of the arch wire in accordance with the inputs to produce a user defined arch wire;
  simulating tooth movement based on the user defined arch wire and the user placed brackets; and
  when the simulating of the tooth movement is not favorable, providing a response requesting alternate inputs for at least one of: generating the arch wire and the placing of the brackets.

29. The apparatus of claim 27, wherein the memory further comprises operational instructions that cause the processing module to:
  determine whether each of the plurality of teeth move along a direct three-dimensional path; and
  when at least one tooth does not move along a corresponding direct three-dimensional path, stage orthodontic treatment in a plurality of tooth movement steps.

30. The apparatus of claim 29, wherein the memory further comprises operational instructions that cause the processing module to:
  when each of the plurality of teeth move along a direct three-dimensional path, determine whether a single arch wire can achieve the desired orthodontic structure; and
  when the single arch wire cannot achieve the desired orthodontic structure, design a series of arch wires.

* * * * *